United States Patent
Groenewegen et al.

(10) Patent No.: US 8,900,612 B2
(45) Date of Patent: Dec. 2, 2014

(54) AMIDES, USE OF AMIDES AS SOLVENTS FOR ORGANIC COMPOUNDS, COMPOSITIONS AND EMULSIONS CONTAINING AMIDES, AND METHOD FOR TREATING A PLANT

(75) Inventors: Adrianus Marinus Groenewegen, Zutphen (NL); Kornelis Overkempe, Holten (NL); Peter Westbye, Stenungsund (SE)

(73) Assignee: Akzo Nobel Chemicals International B.V., Amersfoort (NL)

(*) Notice: Subject to any disclaimer, the term of this patent is extended or adjusted under 35 U.S.C. 154(b) by 0 days.

(21) Appl. No.: 13/518,202

(22) PCT Filed: Dec. 23, 2010

(86) PCT No.: PCT/EP2010/070624
§ 371 (c)(1),
(2), (4) Date: Jul. 26, 2012

(87) PCT Pub. No.: WO2011/080208
PCT Pub. Date: Jul. 7, 2011

(65) Prior Publication Data
US 2012/0283103 A1 Nov. 8, 2012

Related U.S. Application Data

(60) Provisional application No. 61/290,974, filed on Dec. 30, 2009.

(30) Foreign Application Priority Data
Dec. 30, 2009 (EP) .................................... 09180941

(51) Int. Cl.
A01N 25/00 (2006.01)
A01N 25/02 (2006.01)
C07C 233/03 (2006.01)
C07C 233/05 (2006.01)
A01N 25/04 (2006.01)

(52) U.S. Cl.
CPC .............. *C07C 233/03* (2013.01); *A01N 25/02* (2013.01); *C07C 233/05* (2013.01); *A01N 25/04* (2013.01)
USPC ........................................ 424/405; 504/116.1

(58) Field of Classification Search
None
See application file for complete search history.

(56) References Cited

U.S. PATENT DOCUMENTS

| 3,763,236 | A | 10/1973 | Eck et al. |
| 4,217,111 | A | 8/1980 | Frost, Jr. |
| 4,229,374 | A | 10/1980 | Slaugh et al. |
| 4,743,273 | A | 5/1988 | Croudace et al. |
| 4,867,752 | A | 9/1989 | Braid et al. |
| 4,880,576 | A | 11/1989 | Blank et al. |
| 5,206,225 | A | 4/1993 | Horstmann et al. |
| 2003/0050506 | A1 | 3/2003 | Auer et al. |
| 2003/0116423 | A1 | 6/2003 | Auer et al. |
| 2009/0181850 | A1 | 7/2009 | Stern et al. |

FOREIGN PATENT DOCUMENTS

| DE | 1932709 | | 1/1971 |
| FR | 1 168 869 | | 12/1958 |
| WO | WO 88/02216 | | 4/1988 |
| WO | WO 8802216 | * | 4/1988 |
| WO | WO 95/15685 | | 6/1995 |
| WO | WO 01/55070 A2 | | 8/2001 |
| WO | WO 2004/022524 A3 | | 3/2004 |
| WO | WO 2008/101629 A2 | | 8/2008 |
| WO | WO 2008/145063 A1 | | 12/2008 |
| WO | WO 2009/030433 A2 | | 3/2009 |

OTHER PUBLICATIONS

European Search Report dated Apr. 6, 2010, issued in the corresponding European Patent Application No. 09180941.8.
International Search Report mailed Sep. 5, 2011, issued in the corresponding International Application No. PCT/EP2010/070624.
Abstract for Japanese Publication No. JP 57-059805, published Apr. 10, 1982 (XP-002573550).
Abstract for "Homolytic addition of N-alkyl-1-oxa-3azacyclopentanes to terminal olefins," Zhurnal Organicheskoi Khimii, 16(12), 2533-8, 1980 (XP-002573552).
Metayer, "Catalytic hydrogenations of arylalkyl amines on Raney nickel," Ann. Chim., vol. 12, No. 4, pp. 196-257, 1949, (XP-008120452).
Abstract for "Mechanism and applicability of the Guerbet reaction," Chemistry & Industry, pp. 587-591, 1937 (XP-002573825).
Weizmann et al., "Mechanism and applicability of the Guerbet reaction," Chemistry & Industry, pp. 587-591, Jun. 26, 1987 (XP-008120417).
Caplus English Abstract for French Patent Publication 1 168 869, published Dec. 18, 1958.
CAS Registry for Formamide, N-methyl-N-(2-propylheptyl)-, 2009.

* cited by examiner

*Primary Examiner* — Alton Pryor
(74) *Attorney, Agent, or Firm* — Matthew D. Kellam

(57) ABSTRACT

The present invention relates in general to the use of amides of the following general formula (I) wherein $R^1$ is a linear or branched hydrocarbyl group containing 9 to 14 carbon atoms; $R^2$ is selected from the group consisting of methyl, ethyl and benzyl; and $R^3$ is selected from the group consisting of hydrogen, methyl and ethyl, as solvents for organic agriculturally active ingredients, compositions comprising organic agriculturally active ingredients and such amides, methods for treating a plant utilizing such compositions, as well as some of the amides as such and methods for their production.

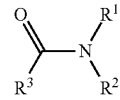

(I)

11 Claims, No Drawings

AMIDES, USE OF AMIDES AS SOLVENTS FOR ORGANIC COMPOUNDS, COMPOSITIONS AND EMULSIONS CONTAINING AMIDES, AND METHOD FOR TREATING A PLANT

CROSS-REFERENCES TO RELATED APPLICATIONS

This application is a National Stage entry of International Application PCT/EP2010/070624, filed Dec. 23, 2010, which claims the benefit of U.S. Patent Application No. 61/290,974 filed Dec. 30, 2009, and European Patent Application No. 09180941.8, filed Dec. 30, 2009. The contents of the aforementioned applications are incorporated herein by reference in their entireties.

TECHNICAL FIELD OF INVENTION

The present invention relates to the use of certain amides as solvents for organic compounds, and to compositions comprising organic agriculturally active ingredients dissolved in the amides. Further, the present invention relates to methods for treating a plant utilizing compositions of the present invention. In addition, the present invention relates to certain amides as such as well as methods for their production.

TECHNICAL BACKGROUND OF THE INVENTION

Organic solvents are commonly used for dissolving organic compounds being water insoluble or having low water solubility. Many agriculturally active ingredients, such as pesticide and plant growth regulators, are organic compounds that commonly are water insoluble, or have low water solubility. Hence, solvents have typically been used in the preparation of agricultural formulations, in order to prepare aqueous agricultural formulations with a concentration of agricultural actives exceeding the solubility thereof in water.

Agricultural formulations are conventionally provided in the form of concentrated compositions, which are diluted with water by the end-user to obtain the work-composition that is eventually used, e.g. sprayed on a crop field. In the case of e.g. water-insoluble agricultural actives, the concentrated composition may be a so-called emulsifiable concentrate which, when mixed with water, results in an emulsion of the agricultural active in water. However, upon dilution of the concentrate with an aqueous medium, the agricultural actives in the emulsion are prone to crystallisation. This is highly undesired, e.g. as such crystals may clog spraying nozzles and/or may result in an uneven distribution of the agricultural active on a field. To meet this problem, recent development has resulted in the use of long-chain dialkyl amides as solvents for agricultural actives.

U.S. Pat. No. 5,206,225 relates to inhibition of crystallisation of specific pesticidally active triazole compounds in sprayable compositions by the addition thereto of alkyl carboxylic acid dimethyl amides based on $C_6$-$C_{20}$ alkyl carboxylic acids. WO 2008/145063 discloses an agrochemical composition that comprises an azole active ingredient and an N,N-dialkyl long chain alkyl amide present in sufficient amount to prevent or inhibit the crystallization of the azole derivative during the application of the composition to a locus. WO 95/15685 relates to the use of carboxylic acid amides as crystallization inhibitors in the application of aqueous sprays that contain certain azole derivatives liable to crystallization.

However, and especially at low temperatures, the crystallisation problem remains to a certain degree with the use of the solvents presented in the above mentioned prior art. Hence, improved organic solvents would be desirable.

SUMMARY OF THE INVENTION

It is an object of the present invention to at least partially overcome the drawbacks of the prior art and to provide organic solvents with a high solvency for water-insoluble organic compounds and organic compounds having a low water solubility, the use of which organic solvents in emulsions further reduces the crystallisation tendency of organic agrochemically active ingredients.

The present inventors have surprisingly found that in view of at least this object, certain amides as further defined herein can advantageously be used as solvents for water-insoluble organic agrochemically active ingredients.

It is to be noted that the present invention relates to all possible combinations of the appended claims.

Hence, in a first aspect, the present invention relates to the use of an amide of the general formula (I)

wherein:
$R^1$ is a linear or branched hydrocarbyl group containing 9 to 14 carbon atoms;
$R^2$ is selected from the group consisting of methyl, ethyl and benzyl; and
$R^3$ is selected from the group consisting of hydrogen, methyl, and ethyl, as a solvent for at least one organic agrochemically active ingredient, preferably selected from the group consisting of a pesticide, a plant growth regulator, and mixtures thereof, preferably such an organic agrochemically active ingredient having low water solubility or being water-insoluble.

In a second aspect, the present invention relates to a composition comprising an amide of general formula (I) as defined herein and at least one organic agrochemically active ingredient, preferably selected from the group consisting of a pesticide, a plant growth regulator, and mixtures thereof, preferably such an organic agrochemically active ingredient having low water solubility or being water-insoluble.

In a third aspect, the present invention relates to a method of treating a plant, comprising contacting said plant with a composition of the present invention.

In a fourth aspect, the present invention relates to an amide of the general formula (I)

wherein:
$R^1$ is 2-propylheptyl;
$R^2$ is selected from the group consisting of methyl, ethyl and benzyl; and $R^3$ is selected from the group consisting of hydrogen, methyl, and ethyl; and to the production of such amides.

These and other aspects of the present invention are described more in detail below.

DETAILED DESCRIPTION OF THE INVENTION

The present invention relates in general to the use of amides of the following general formula (I)

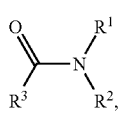

as solvents for at least one organic agrochemically active ingredient, preferably an agrochemically active ingredient having low water solubility or being water insoluble.

In the general formula (I):

$R^1$ is a linear or branched hydrocarbyl, preferably alkyl, group containing from 9, preferably from 10, to 14, preferably to 12 carbon atoms. Preferred examples of $R^1$ groups include 2-propylheptyl, n-decyl, iso-decyl and monomethyl substituted $C_{9-10}$ alkyls. 2-propylheptyl and n-decyl are more preferred, and 2-propylheptyl is most preferred.

$R^2$ is selected from the group consisting of methyl, ethyl and benzyl, preferably methyl.

$R^3$ is selected from the group consisting of hydrogen, methyl and ethyl, preferably hydrogen or methyl.

Preferred amides of the general formula (I) for use in the present invention include, but are not limited to, N-methyl-N-(2-propylheptyl)-formamide, N-methyl-N-(2-propylheptyl)-acetamide, N-methyl-N-(n-decyl)-acetamide, N-methyl-N-(n-decyl)-formamide, N-methyl-N-(monomethyl substituted $C_{9-10}$ alkyl)-acetamide and N-methyl-N-(monomethyl substituted $C_{9-10}$alkyl)-formamide, more preferably N-methyl-N-(2-propylheptyl)-formamide, N-methyl-N-(2-propylheptyl)-acetamide and N-methyl-N-(n-decyl)-formamide.

As such, amides of the general formula (I) above, wherein $R^1$ is 2-propylheptyl, $R^2$ is is selected from the group consisting of C1-4 hydrocarbyl groups, arylgroups, C1-4 hydrocarbylsubstituted arylgroups and the benzyl group, preferably from the group consisting of methyl, ethyl and benzyl, most preferably methyl, and $R^3$ is hydrogen, methyl or ethyl, preferably hydrogen or methyl, and their production represent separate aspects of the present invention.

Amides of the general formula (I) may, inter alia, be synthesized according to the following general method.

In a first reaction, an alcohol of formula $R^1$—OH is reacted with an amine of formula $R^2$—$NH_2$ to form an amine of formula $(R^1)(R^2)NH$. Reaction conditions for this first reaction will be apparent to the skilled person, and the reaction can inter alia be performed according to the teaching of U.S. Pat. No. 4,229,374.

In a second reaction, the amine $(R^1)(R^2)NH$ is then reacted with a carboxylic acid of the general formula $R^3$—COOH, or a derivative thereof, such as an anhydride or acid chloride of the carboxylic acid, to result in an amide of the general formula (I). Reaction conditions for this second reaction will be apparent to the skilled person, and the reaction can inter alia be performed according to the teaching of March, J "Advanced Organic Chemistry: Reactions, Mechanisms, and Structure" 1968, McGraw-Hill Kogakusha, Ltd, reaction "0-53" on page 336.

In connection to the first reaction, it is to be mentioned that alcohols of formula $R^1$—OH may be in pure form, i.e. essentially only containing one product, or may be in the form of a mixture of several alcohols. One example of such a mixture of several alcohols is the product Neodol® 91 from Shell Chemicals, which is a mixture containing about 80 wt % linear $C_{9-11}$ alcohols and about 20 wt % of monomethyl substituted $C_8$, $C_9$ and $C_{10}$ alcohols.

The organic agrochemically active ingredients contemplated for use in the present invention are preferably selected amongst those having low water solubility, and most preferably amongst those being water insoluble. The organic agriculturally active ingredients contemplated for use in the present invention, also referred to in the art as agricultural actives, are preferably selected from the group consisting of pesticides and plant growth regulators The term "organic agrochemically active ingredient" as used herein is to be taken as encompassing any organic compound being agrochemically active, except for amides of the general formula (I) and emulsifying agents as defined herein, should any of these be agriculturally active.

The term "compound having low water solubility" as defined herein, relates to a compound having a solubility of at most 5, preferably at most 1 Wl, in water.

The term "compound being water insoluble" as defined herein, relates to a compound which has a solubility of at most 0.2, preferably at most 0.1, more preferably at most 0.05, and most preferably at most 0.040 g/l in water.

In the context of the present invention, water solubility shall be interpreted as being measured according to ASTM E 1148-87 "Standard Test Method for Measurements of Aqueous Solubility".

As used herein, the term "pesticide" refers to an organic compound that will prevent, destroy, repel, or mitigate any pest.

As used herein, the term "plant growth regulator" refers to an organic compound, which through physiological action will accelerate or retard the rate of growth or rate of maturation or otherwise alter the behaviour of ornamental or crop plants or the products thereof.

Pesticides contemplated for use in the present invention include, but are not limited to, fungicides, herbicides, insecticides, miticides, nematicides, acaricides, and molluscicides.

Preferred agriculturally active ingredients contemplated for use in the present invention include, but are not limited to pesticides and plant growth regulators of the classes triazoles, strobilurins, alkylenebis(dithiocarbamate) compounds, benzimidazoles, phenoxy carboxylic acids, benzoic acids, sulfonylureas, triazines, pyridine carboxylic acids, neonicotinides, amidines, organophosphates, and pyrethroids.

Examples of fungicides contemplated for use in the present invention include, but are not limited to, fungicides of the classes triazoles (e.g. tebuconazole, tetraconazole, cyproconazole, epoxiconazole, difenconazole, propiconazole, prothioconazole), strobilurins (e.g. trifloxystrobin, azoxystrobin, fluoxastrobin, pyraclostrobin), alkylenebis (dithiocarbamate) compounds (e.g. mancozeb) and benzimidazoles (e.g. carbendazim).

Examples of herbicides contemplated for use in the present invention include, but are not limited to, phenoxy carboxylic acids (e.g. 2,4-D-acid), benzoic acids (e.g. Dicamba-acid), sulfonylureas (e.g. methylsulfuron-methyl, rimsulfuron), triazines (e.g. atrazine and simazine) and pyridine carboxylic acids (e.g. triclopyr).

Examples of insecticides contemplated for use in the present invention include, but are not limited to, neonicotinides (e.g. thiachloprid, acetamiprid), amidines (e.g. amitraz), organophosphate (e.g. chlorpyrifos) and pyrethroids (e.g. permethrin, bifenthrin, deltamethrin).

For a detailed description of each of the above mentioned pesticides and plant growth regulators, reference is made to handbooks, e.g. "The e-Pesticide Manual v4.0" from BCPC Publications Ltd, Alton, Hampshire. (ISBN 1 901396 42 8)

The amides of general formula (I) may advantageously be used as solvents for many organic compounds in addition to agriculturally active ingredients. Hence, the use of an amide of general formula (I), as defined above, as a solvent for at least one organic compound, preferably having low water solubility, more preferably being water-insoluble, as defined above, is also contemplated as a separate aspect of the present invention.

It is to be noticed that also mixtures of two or more different amides of the general formula (I) are contemplated as a solvent in accordance with the present invention.

The amides of general formula (I) can be used to solubilise up to for example 800 g of such an organic agriculturally active ingredient in a final volume of 1 liter.

The present invention also relates to a composition comprising at least one organic agriculturally active ingredient, preferably having low water solubility, more preferably being water-insoluble, as mentioned above, and an amide of the general formula (I) as defined above. Preferably, the at least one organic agrochemically active ingredient is at least partially, more preferably fully, dissolved in the amide of general formula (I).

The concentration of such one or more organic agrochemically active ingredient in a composition of the present invention is typically within the solubility range of the specific compound in the specific amide. The concentration of the at least one organic agrochemically active ingredient in such a composition is from at least more than 0, preferably from at least 10, and most preferably from at least 50 g/l, to at most about 800 g/l, preferably at most about 500 g/l, and most preferably at most about 300 g/l based on the combined volume of organic agrochemically active ingredient and amide of the general formula (I). In a representative composition of the present invention, the concentration of the at least one organic agrochemically active ingredient in such a composition is about 250 g/l.

In one embodiment, the composition of the present invention is an emulsifiable concentrated composition, hereinafter and in the art commonly referred to as an "emulsifiable concentrate", comprising a composition as defined herein, and further comprising an emulsifying agent. Hence, such an emulsifiable concentrate comprises an amide of the general formula (I) as defined herein, at least one organic agrochemically active ingredient, preferably having low water solubility, more preferably being water-insoluble, as defined herein, and an emulsifying agent.

In an emulsifiable concentrate, the concentration of active ingredients, such as the organic agrochemically active ingredient dissolved in the amide of general formula (I) is typically too high for end-use, and the emulsifiable concentrate is intended to be diluted with an aqueous medium into a work-composition.

In one embodiment, the emulsifiable concentrate preferably comprises water in an amount at which an emulsion is not formed. Preferably, the emulsifiable concentrate comprises less than about 10, more preferably less than about 1 wt % of water, based on the total weight of the emulsifiable concentrate. Most preferably, the emulsifiable concentrate of the present invention is essentially free from water in the sense that the emulsifiable concentrate does not contain water beyond what is inevitable from the equilibrium with the surrounding atmosphere.

In another embodiment, the emulsifiable concentrate is in the form of an emulsion, but where the concentration of the at least one organic agrochemically active ingredient is significantly higher than the concentration intended for the end-use, i.e. the emulsifiable concentrate must be diluted significantly before the intended end use.

The emulsifiable concentrate of the present invention is typically so formulated that when added to an aqueous medium, or when an aqueous medium is added to the emulsifiable concentrate, an emulsion is formed, preferably where the at least one organic agrochemically active ingredient is dissolved in the amide of general formula (I), and this solution is emulsified in the aqueous medium.

The emulsifying agent is comprised in the emulsifiable concentrate in a concentration sufficient for an emulsion to form when the emulsifiable concentrate is mixed with an aqueous medium. The optimum concentration of the emulsifying agent will depend on the type of emulsifying agent used and the species of amide of general formula (I). Typically the emulsifying agent is present in a concentration of from at least about 10, preferably at least about 30, and most preferably at least about 60, to at most about 250, preferably at most about 150, and most preferably at most about 100 g of emulsifying agent per liter of the emulsifiable concentrate.

Emulsifying agents contemplated for use in the present invention include surfactants known as emulsifying agents by those skilled in the art, such as, but not limited to, anionic surfactants, non-ionic surfactants, polymers, and blends of two or more thereof, especially blends comprising anionic and non-ionic surfactants.

Examples of anionic surfactants contemplated for use alone or in combination as emulsifying agent include Ca/NaDDBS (calcium or sodium dodecylbenzene sulphonate), sulfosuccinates and phosphate esters.

Examples of nonionic surfactants for use alone or in combination as emulsifying agent include alcohol alkoxylates, tristyrylphenol alkoxylates, castor oil alkoxylates and alkyl glycosides.

Examples of polymers for use alone or in combination as emulsifying agent include ethylene oxide-propylene oxide block co-polymers, acrylic acid based comb polymers, and xanthan gum.

The present invention also relates to an aqueous emulsion comprising an aqueous medium, an emulsifying agent, at least one organic agrochemically active ingredient, preferably having low water solubility, more preferably being water-insoluble, and an amide of general formula (I). Preferably, the at least one organic agrochemically active ingredient is dissolved in the amide of general formula (I) and this solution is emulsified in the aqueous medium.

For example, such an emulsion may be obtained by mixing an aqueous medium and an emulsifiable concentrate as previously defined herein, or by mixing an aqueous medium with the amide of general formula (I), the at least one organic agrochemically active ingredient and the emulsifying agent.

As used herein, the term "emulsion" shall be interpreted to include macro emulsions, micro emulsions and suspoemulsions, i.e. emulsions in which a particulate solid is suspended.

The aqueous medium that is a component of the emulsion of the present invention typically comprises water as the major component. Preferably, water constitutes at least 50 wt % such as at least 75 wt %, for example at least 90 wt % of the aqueous medium. The aqueous medium may further comprise other components, such as, but not limited to salts, buffering agents, pH-controlling agents, such as acids or bases, fertilizers, etc.

When the emulsifiable concentrate is mixed with the aqueous medium, an emulsion, preferably a stable emulsion is formed, the emulsion typically being the work composition that will be used by the end-user, with the advantage that the end-user does not have to handle and store large quantities of work composition, but can prepare the amounts necessary for the moment.

Emulsions of the present invention typically have a volume ratio between formulation and aqueous medium of from about 1:50, preferably from about 1:100, more preferably from about 1:200; to about 1:1000, preferably to about 1:500, more preferably to about 1:300, where "formulation" represents the combination of amide of general formula (I), organic agrochemically active ingredient dissolved therein and emulsifying agent, i.e. the formulation can represent the emulsifiable concentrate or the components of such emulsifiable concentrate. In a representative emulsion of the present invention, the volume ratio formulation:aqueous medium is about 1:200.

An advantage of the present invention is that even at high dilutions in the emulsion, i.e. at low ratios between the formulations and the aqueous medium, the tendency of the water insoluble organic agrochemically active ingredient dissolved in the amide of general formula (I) to crystallize is low, also at temperatures significantly below room temperature, such as at 5° C. This is advantageous for many reasons. For instance, an emulsion of the present invention will be possible to spray also in cold conditions, such as at or around 5° C., as the compositions show no tendencies to form crystals. Further, should it be necessary for the end-user to stop spraying before having consumed a full batch of emulsion, the unused emulsion will be possible to use later, for example the next day, even if the unused emulsion was stored at reduced temperatures.

A method for treating a plant represents a separate aspect of the present invention. Such a method comprises the step of contacting said plant with a composition or an emulsion of the present invention. Preferably, the contacting of the plant is made by means of spraying. In the composition or emulsion used in the method of the present invention for treating a plant, the agrochemically active ingredient is preferably dissolved in the amide of general formula (I). In the emulsion used in the method of the present invention for treating a plant, the agrochemically active ingredient is dissolved in the amide of general formula (I), and this solution is emulsified in the aqueous medium.

An emulsion of the present invention may be provided as such, or its components may be provided separately. Hence, a kit of parts comprising (a) an amide of the general formula (I) as defined herein; (b) an emulsifying agent; and (c) at least one organic agrochemically active ingredient, preferably an organic agrochemically active ingredient having low water solubility or being water-insoluble, wherein in said kit of parts (a) and (b), (a) and (c), or (b) and (c) optionally may be available as a combination, represents a separate aspect of the present invention.

Those skilled in the art will realise that additional components apart from the amide of general formula (I), the at least one organic agrochemically active ingredient and the emulsifying agent may be present in the composition of the present invention, the emulsifiable concentrate of the present invention or the emulsion of the present invention. Examples of such additional components include for example adjuvants, such as bioefficacy enhancers that are conventionally used to increase the bioefficacy of agricultural actives. Such additional components may be present in the composition or the emulsifiable concentrate of the present invention, or may be present in the aqueous medium with which an emulsifiable concentrate is mixed to form an emulsion of the present invention, or may be added separately to an emulsion of the present invention.

EXPERIMENTS

Example 1

Synthesis of
N-methyl-N-(2-propylheptyl)-formamide

A total amount of 846 g (4.81 moles) of N-methyl-N-(2-propylheptyl)-amine was added to a 2 l round bottomed flange flask equipped with a condenser. Formic acid was charged into a dropping funnel in an amount of 223.3 g (4.80 moles) and added drop wise to the round bottomed flange flask over a time period of 1 hour during heating and stirring with a magnetic stirrer. The final temperature was set to 180° C., while the boiling point of the initial reaction mixture was ~125° C. Water was distilled off and collected in a round bottomed receiver flask and thereby removed from the reaction medium. During the reaction the boiling point of the reaction medium rose continuously. The reaction was performed at atmospheric pressure for a total time of 3.5 hours. Titration of remaining amine was performed to monitor the reaction. When the amine value did not decrease anymore, the remaining unreacted material was removed by gently pulling vacuum to 100 mbar for two hours. The reaction mixture was cooled to 60° C. before breaking the vacuum.

$^1$H-NMR of the product dissolved in $CDCl_3$ was recorded on a Varian INOVA spectrometer with a proton resonance frequency of 400 MHz, using a 5 mm 4NQ-probe. The NMR shift values are summarized in table 1 below.

TABLE 1

NMR shifts in $^1$H-NMR spectrum of N-methyl-N-(2-propylheptyl)-formamide

| δ(ppm) | Peak |
|---|---|
| 0.87 | Multiplet |
| 1.25 | Multiplet |
| 1.68 | Multiplet |
| 2.82 and 2.92 | 2 singlets |
| 3.10 and 3.23 | 2 doublets |
| 8.03 | 2 singlets |

The product was diluted to a concentration of about 20 ppm in dichloromethane and injected into a Gas Chromatograph-Mass Spectrometer (Thermo Trace GCMS) with an injection temperature of 200° C. Helium was used as carrier gas at a flux of 0.8 mL/min and the separation took place in a capillary column (HP-1 ms). N-methyl-N-(2-propylheptyl)-formamide was seen at 15.41 min in the GC spectra and a peak was seen at 199 m/z in the MS spectra.

The boiling point of the N-methyl-N-(2-propylheptyl)-formamide was 287° C. as measured by differential scanning calorimetry (Mettler Toledo, DCS1) and evaluated using STARe software (Mettler Toledo).

Example 2

Synthesis of
N-methyl-N-(2-propylheptyl)-acetamide

The same experimental procedure as in Example 1 was used, using acetic acid anhydride instead of formic acid. A total amount of 584.2 g (3.32 moles) of N-methyl-N-(2-propylheptyl)-amine was reacted with 169.6 g (1.66 moles) of acetic acid anhydride. The reaction was performed at atmospheric pressure for a total time of 14.5 hours.

$^1$H-NMR of the product dissolved in CDCl$_3$ was recorded on a Varian VNMRS 400 spectrometer with a proton resonance frequency of 400 MHz, using a 5 mm 4NQ-probe. The NMR shift values are summarized in table 2 below.

TABLE 2

NMR shifts in $^1$H-NMR spectrum of N-methyl-N-(2-propylheptyl)-acetamide

| δ(ppm) | Peak |
|---|---|
| 0.90 | Multiplet |
| 1.25 | Multiplet |
| 1.68 | Multiplet |
| 2.09 | Singlet |
| 2.89 and 2.96 | 2 singlets |
| 3.15 and 3.28 | 2 doublets |

The same procedure for Gas Chromatograph-Mass Spectrometer as in Example 1 was used. N-methyl-N-(2-propylheptyl)-acetamide was seen at 15.97 min in the GC spectra and a peak was seen at 213 m/z in the MS spectra.

The boiling point of the N-methyl-N-(2-propylheptyl)-acetamide was 291° C. as measured by differential scanning calorimetry (Mettler Toledo, DCS1) and evaluated using STARe software (Mettler Toledo).

Example 3

Solubility of Active Ingredients

Various agriculturally active ingredients were dissolved in both N-methyl-N-(2-propylheptyl)-formamide and N-methyl-N-(n-decyl)-formamide in order to evaluate the solubility of the active ingredients in the amides.

This was done by adding the active ingredient (AI) to a beaker and thereafter adding the solvent until the entire AI had been dissolved. The solutions were continually stirred at a temperature of 23° C. during the experiments. When everything had been dissolved, the beakers were left without stirring for 24 h to see if the solution was stable (i.e. no crystallization).

As a reference, the solubility of the active ingredients in water, the numbers taken from the e-Pesticide Manual v 4.0, supra, are also listed.

TABLE 3

Dissolution of active ingredients into N-methyl-N-(2-propylheptyl) formamide and N-methyl-N-(n-decyl) formamide measured as grams of AI in 100 g solvent.

Solubility (g AI/100 g solvent)

| Active ingredient (AI) | N-Methyl-N-(2-propylheptyl) formamide | N-Methyl-N-(n-decyl) formamide | Water |
|---|---|---|---|
| Tebuconazole | 48 | 48 | 0.0036 |
| Difenoconazole | 38 | 38 | 0.0015 |
| Trifloxystrobin | 23 | 23 | 0.000061 |
| 2,4-D acid | 41 | >50 | 0.0311 |
| Amitraz | >50 | >50 | <0.00001 |
| Bifenthrin | >50 | >50 | <0.0000001 |

Example 4

Emulsion Dilution

Formulations containing 250 g/l of tebuconazole was formulated together with 100 g/l of surfactant blend (CaDDBS and tristyrylphenol ethoxylate (15 EO), 50:50) and diluted to a final volume of one liter with each one of the solvents N,N-dimethyl decanamide, N-methyl-N-octyl propanamide, N-methyl-N-(2-propylheptyl) formamide or N-methyl-N-(n-decyl) formamide. Each formulation was emulsified into tap water at ambient temperature (~22° C.) in the volume ratio (formulation:water) 1:100, 1:150, 1:200 and 1:500 dilution. The emulsions were poured into 100 ml conical glass centrifuge tubes and monitored over time at three different temperatures 5, 20 and 40° C. for observation of crystallisation of active ingredient (tebuconazole).

Crystallization was judged by ocular inspection with the naked eye, and in the table below, the following is used:
+ no crystals visible,
− crystals visible.

TABLE 4

Crystallisation of tebuconazole in emulsions of N,N-dimethyl decanamide, N-methyl-N-octyl propanamide N-methyl-N-(2-propylheptyl) formamide or N-methyl-N-(n-decyl) formamide over time in tap water.

Emulsions at 5° C.

| Time (h) | N,N-dimethyl decanamide (reference) | | | | N-methyl-N-octyl propanamide (reference) | | | | N-methyl-N-(2-propylheptyl) formamide | | | | N-methyl-N-(n-decyl) formamide | | | |
|---|---|---|---|---|---|---|---|---|---|---|---|---|---|---|---|---|
| | 1:100 | 1:150 | 1:200 | 1:500 | 1:100 | 1:150 | 1:200 | 1:500 | 1:100 | 1:150 | 1:200 | 1:500 | 1:100 | 1:150 | 1:200 | 1:500 |
| 3 | + | + | + | + | + | + | + | + | + | + | + | + | + | + | + | + |
| 6 | + | + | + | − | + | + | + | − | + | + | + | + | + | + | + | + |
| 12 | + | + | − | − | + | + | − | − | + | + | + | + | + | + | + | + |
| 24 | + | − | − | − | + | + | − | − | + | + | + | + | + | + | + | + |
| 36 | + | − | − | − | + | + | − | − | + | + | + | + | + | + | + | + |
| 48 | + | − | − | − | + | − | − | − | + | + | + | + | + | + | + | + |
| 72 | + | − | − | − | + | − | − | − | + | + | + | + | + | + | + | + |
| 96 | + | − | − | − | + | − | − | − | + | + | + | + | + | + | + | + |

At 20 and 40° C., crystallization was not visible for any of the emulsions.

The invention claimed is:

1. A method for solubilizing or dissolving an organic agrochemically active ingredient, the method comprising combining the organic agrochemically active ingredient with an amide of the general formula (I)

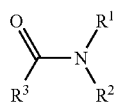

(I)

wherein:
R¹ is a linear or branched hydrocarbyl group containing 9 to 12 carbon atoms;
R² is selected from the group consisting of methyl and benzyl; and
R³ is selected from the group consisting of hydrogen.

2. The method of claim 1, wherein said organic agrochemically active ingredient is selected from the group consisting of a pesticide, a plant growth regulator, or mixtures thereof.

3. The method according to claim 1, wherein R¹ is selected from the group consisting of 2-propylheptyl, 2-butyloctyl, isodecyl, n-decyl and monomethyl substituted $C_{9-10}$ alkyls.

4. The according to claim 3, wherein R¹ is 2-propylheptyl and R² is methyl.

5. The method according to claim 1, wherein said organic agriculturally active ingredient is a pesticide or plant growth regulator selected from the group consisting of triazoles, strobilurins, benzimidazoles, phenoxy carboxylic acids, benzoic acids, sulfonylureas, pyridine carboxylic acids, neonicotinides, amidines, pyrethroids and mixtures of two or more thereof.

6. A composition comprising at least one organic agriculturally active ingredient selected from the group consisting of a pesticide, a plant growth regulator, and mixtures thereof, and an amide of the general formula (I)

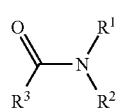

(I)

wherein:
R¹ is a linear or branched hydrocarbyl group containing 9 to 12 carbon atoms;
R² is selected from the group consisting of methyl and benzyl; and
R³ is selected from the group consisting of hydrogen.

7. The composition according to claim 6, wherein said organic agriculturally active ingredient is selected from the group consisting of a pesticide, a plant growth regulators and mixtures thereof.

8. The composition according to claim 6, wherein said pesticide or plant growth regulator is selected from the group consisting of triazoles, strobilurins, benzimidazoles, phenoxy carboxylic acids, benzoic acids, sulfonylureas, pyridine carboxylic acids, neonicotinides, amidines, pyrethroids and mixtures thereof.

9. The composition according to claim 6, further comprising an emulsifying agent.

10. The composition according to claim 9, said composition being an emulsion.

11. A method for the treatment of a plant, comprising contacting said plant with a composition according to claim 6.

* * * * *